(12) United States Patent
Jhaveri et al.

(10) Patent No.: US 11,357,597 B2
(45) Date of Patent: Jun. 14, 2022

(54) METHOD AND SYSTEM FOR DATA EXCHANGE WITH ROBOTIC SURGICAL TOOLS USING NEAR FIELD COMMUNICATION (NFC)

(71) Applicant: Verb Surgical Inc., Santa Clara, CA (US)

(72) Inventors: Mufaddal Jhaveri, Fremont, CA (US); Robert Abad, Santa Clara, CA (US); Jan Bosteels, San Jose, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

(21) Appl. No.: 16/792,705

(22) Filed: Feb. 17, 2020

(65) Prior Publication Data

US 2021/0251720 A1 Aug. 19, 2021

(51) Int. Cl.
*G06K 7/10* (2006.01)
*G06K 19/07* (2006.01)
(Continued)

(52) U.S. Cl.
CPC .............. *A61B 90/98* (2016.02); *A61B 34/30* (2016.02); *G06K 7/10297* (2013.01);
(Continued)

(58) Field of Classification Search
CPC ................... A61B 90/98; A61B 34/30; A61B 2017/00221; A61B 2017/00464;
(Continued)

(56) References Cited

U.S. PATENT DOCUMENTS

2005/0222566 A1* 10/2005 Nakahira ............... A61B 18/14
606/41
2011/0291803 A1 12/2011 Bajic et al.
(Continued)

FOREIGN PATENT DOCUMENTS

KR 10-2010-0008878 1/2010

OTHER PUBLICATIONS

International Search Report and Written Opinion for International Application No. PCT/US2020/020822 dated Nov. 11, 2020, 11 pages.

*Primary Examiner* — Michael G Lee
*Assistant Examiner* — David Tardif
(74) *Attorney, Agent, or Firm* — Womble Bond Dickinson (US) LLP

(57) ABSTRACT

In this patent disclosure, various embodiments of using near-field communication (NFC) to facilitate the transfer of data and power between a robotic surgical system and a surgical tool attached to the robotic surgical system are disclosed. In one aspect, a process for automatically managing surgical tool attachment in a robotic surgical system can begin by detecting an attachment of a surgical tool. The process next establishes a secure near-field communication (NFC) link between a first NFC module embedded in the robotic surgical system and a second NFC module embedded in the surgical tool. Next, the process requests tool calibration data from the surgical tool via the secure NFC link. The process subsequently uses the received tool calibration data to initialize the surgical tool so that the surgical tool is ready for use.

20 Claims, 7 Drawing Sheets

(51) Int. Cl.
  *A61B 90/98* (2016.01)
  *A61B 34/30* (2016.01)
  *A61B 17/00* (2006.01)
(52) U.S. Cl.
  CPC ..... *G06K 19/0705* (2013.01); *G06K 19/0723* (2013.01); *A61B 2017/00221* (2013.01); *A61B 2017/00464* (2013.01); *A61B 2017/00725* (2013.01)
(58) Field of Classification Search
  CPC ..... A61B 2017/00725; G06K 7/10297; G06K 19/0705; G06K 19/0723
  USPC .......................................................... 606/1
  See application file for complete search history.

(56) References Cited

U.S. PATENT DOCUMENTS

| | | | |
|---|---|---|---|
| 2015/0083781 A1* | 3/2015 | Giordano | A61B 17/07207 227/176.1 |
| 2017/0360520 A1 | 12/2017 | Hares | |
| 2018/0168763 A1 | 6/2018 | Scheib et al. | |
| 2019/0247133 A1 | 8/2019 | Overmyer et al. | |
| 2019/0374292 A1* | 12/2019 | Barral | A61B 34/30 |
| 2020/0084029 A1* | 3/2020 | Yang | H04L 63/061 |
| 2020/0405440 A1* | 12/2020 | Shelton, IV | A61B 90/96 |

\* cited by examiner

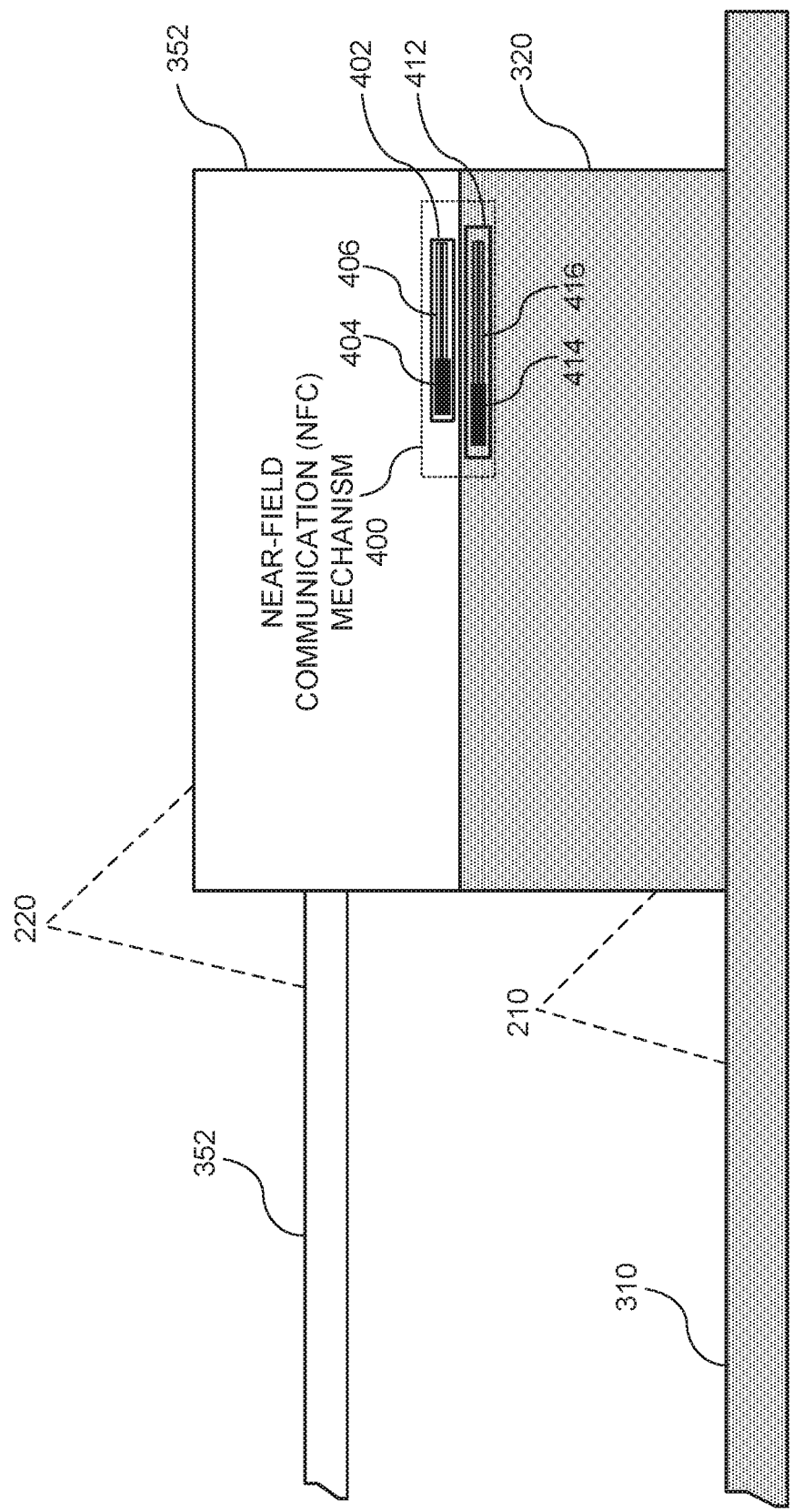

METHOD AND SYSTEM FOR DATA EXCHANGE WITH ROBOTIC SURGICAL TOOLS USING NEAR FIELD COMMUNICATION (NFC)

TECHNICAL FIELD

The present disclosure generally relates to robotic surgery platforms and, more specifically, to systems, devices and techniques for automatically establishing secure communication links/channels between a newly-attached robotic surgical tool and robotic surgery platform.

BACKGROUND

During a robotic surgical procedure on a robotic surgical platform, surgical instruments/tools can be attached to or removed from a robot arm on the basis of individual tool need, as each surgical tool is often designed to accomplish a specific surgical function. Notably, each of these surgical tools is controlled by the surgical robot in a specific manner. This means that the surgical robot needs to be aware of the type of surgical tool attached to the robot arm and also needs to obtain the tool-specific parameters which are needed to control an attached surgical tool. Generally speaking, each surgical tool needs to convey tool-specific information, such as tool identify information, and tool-specific parameters, such as parameters needed to control the tool to the surgical robot when the tool is attached to the surgical robot. The surgical tool may store such information and parameters on the tool itself. However, in order for the surgical robot to retrieve this data from an attached surgical tool, a source of power on the tool and a communication channel between the surgical tool and the surgical robot would be required.

However, the surgical robot and the attached surgical tool are typically separated by a sterile barrier. This sterile barrier, such as an autoclave wraps around the body of the tool for reuse purposes, and only a port of the tool that extends beyond the sterile barrier is involved in surgical action. Moreover, the surgical tool is typically electrically passive which means the tool does not have a source of power. Unfortunately, conventional interconnects include serial ports, Ethernet, and or other wire connections are not desirable communication options between the surgical tool and the surgical robot because they require an open connection which would violate the sealed nature of the surgical tool.

SUMMARY

This patent disclosure provides various embodiments of using near-field communication (NFC) to facilitate the transfer of data and power between a robotic surgical system and a surgical tool attached to the robotic surgical system. More specifically, NFC modules, such as an NFC tag and an NFC reader can be respectively embedded in the surgical tool and the surgical robot, wherein each NFC modules can further include a microcontroller and a memory. Using the NFC modules, an NFC communication link can be established between the surgical robot and the surgical tool, so that data and power can be transmitted from the NFC module embedded in the surgical robot to the NFC module embedded in the surgical tool. The NFC module in the surgical tool, once booted up will be ready to respond to the data request from the surgical robot through the established NFC communication link (or "NFC link").

In one aspect, a process for automatically managing surgical tool attachment in a robotic surgical system is disclosed. This process can begin by detecting an attachment of a surgical tool. The process next establishes a secure near-field communication (NFC) link between a first NFC module embedded in the robotic surgical system and a second NFC module embedded in the surgical tool. Next, the process requests tool calibration data from the surgical tool via the secure NFC link. The process subsequently uses the received tool calibration data to initialize the surgical tool so that the surgical tool is ready for use.

In some embodiments, the process establishes the secure NFC link between the first NFC module in the robotic surgical system and the second NFC module in the surgical tool by first enabling the first NFC module, wherein the first NFC module when enabled, supplies wireless power to the second NFC module in the surgical tool. The process then transmits a NFC link initiation request to the second NFC module; and subsequently receives, at the robotic surgical system, a NFC link initiation response from the second NFC module in response to the NFC link initiation request.

In some embodiments, after establishing the secure NFC link, the process further includes performing a certificate validation procedure between the robotic surgical system and the surgical tool to validate both an authenticity of the robotic surgical system to the surgical tool and an authenticity of the surgical tool to the robotic surgical system.

In some embodiments, the process performs the certificate validation procedure between the robotic surgical system and the surgical tool by first providing a robot certificate to the surgical tool encrypted with a first public key of the robotic surgical system via the secure NFC link. Next, at the surgical tool, the process further includes the steps of: decrypting the encrypted robot certificate with a first matching private key of the surgical tool; comparing the received robot certificate with a robot ID stored in the second NFC module to verify if the received robot certificate matches the stored robot ID; and if so, confirming the authenticity of the robotic surgical system. Otherwise, if the received robot certificate does not match the stored robot ID, the process generates a first authentication error indicating a failure of the certificate validation procedure.

In some embodiments, if the authenticity of the robotic surgical system is confirmed, the process then sends a tool certificate to the robotic surgical system encrypted with a second public key of the surgical tool via the secure NFC link. Next, at the robotic surgical system, the process further includes the steps of: decrypting the encrypted tool certificate with a second matching private key of the robotic surgical system; comparing the received tool certificate with a tool ID stored on the robotic surgical system to verify if the received tool certificate matches the stored tool ID; and if so, confirming the authenticity of the surgical tool, thereby completing the certificate validation procedure between the robotic surgical system and the surgical tool. Otherwise, if the received tool certificate does not match the stored tool ID, the process generates a second authentication error indicating a failure of the certificate validation procedure.

In some embodiments, after validating the authenticities of the robotic surgical system and the surgical tool, the process further includes performing a session key procedure to establish a session key between the robotic surgical system and the surgical tool for secure data exchange between the robotic surgical system and the surgical tool via the secure NFC link.

In some embodiments, the process performs the session key procedure to establish a session key between the robotic surgical system and the surgical tool by: generating a crypto challenge and a first session key; transmitting the crypto challenge unencrypted to the surgical tool via the secure NFC link; receiving, from the surgical tool, an encrypted crypto challenge encrypted with a second session key generated by the surgical tool; attempting to decrypt the received encrypted crypto challenge with the first session key; and if the decrypted crypto challenge matches the crypto challenge, establishing the first session key or the second session key as a mutual session key for encrypting data exchange between the surgical robot and the surgical tool. Otherwise, if the decrypted crypto challenge does not match the crypto challenge, the process triggers an authentication error indicating a failure of the session key procedure.

In some embodiments, the crypto challenge includes a random number.

In some embodiments, prior to requesting the tool calibration data from the surgical tool, the process further includes the steps of: requesting tool usability information and a tool use count from the second NFC module via the secure NFC link; determining if the surgical tool is usable based on the received tool usability information; and if the received tool usability information indicates that the surgical tool is unusable, triggering a tool identification error indicate a failure to initialize the surgical tool.

In some embodiments, if the received tool usability information indicates that the surgical tool is usable, the process further includes checking to determine if the surgical tool has been previously used in the surgical procedure. If so, the process then retrieves tool calibration data directly from a cache of the robotic surgical system and subsequently uses the retrieved tool calibration data to initialize the surgical tool so that the surgical tool is ready for use in the surgical procedure.

In some embodiments, if it is determined that the surgical tool has not been used in the surgical procedure, the process further includes decrementing the received use count of the surgical tool and updating the use count of the surgical tool in the second NFC module via the established secure NFC link.

In some embodiments, the first NFC module includes an NFC reader, and wherein the second NFC module includes an NFC tag.

In some embodiments, after initializing the surgical tool, the process further includes powering down the first NFC module and the second NFC module to save power.

In another aspect, a robotic surgical system is disclosed. This robotic surgical system can includes a robot arm and a first NFC module embedded in the robot arm. The robotic surgical system further includes one or more processors configured to: detect a surgical tool mechanically coupled to the robot arm; establish a near-field communication (NFC) link between the first NFC module embedded in the robot arm and a second NFC module embedded in the surgical tool; and initialize the surgical tool using tool calibration data received from the surgical tool via the established NFC link.

In some embodiments, the one or more processors are configured to establish the NFC link between the first NFC module in the robotic surgical system and the second NFC module in the surgical tool by: enabling the first NFC module, wherein the first NFC module when enabled, supplies wireless power to the second NFC module in the surgical tool; transmitting a NFC link initiation request to the second NFC module; and receiving, at the robotic surgical system, a NFC link initiation response from the second NFC module in response to the NFC link initiation request.

In some embodiments, the one or more processors are further configured to perform a session key procedure to establish a session key between the robotic surgical system and the surgical tool by: generating a crypto challenge and a first session key; transmitting the crypto challenge unencrypted to the surgical tool via the established NFC link; receiving, from the surgical tool, an encrypted crypto challenge encrypted with a second session key generated by the surgical tool; attempting to decrypt the received encrypted crypto challenge with the first session key; and (1) if the decrypted crypto challenge matches the crypto challenge, establishing the first session key or the second session key as a mutual session key for encrypting data exchange between the surgical robot and the surgical tool, (2) otherwise, if the decrypted crypto challenge does not match the crypto challenge, triggering an authentication error indicating a failure of the session key procedure.

In some embodiments, the one or more processors are further configured to: request tool usability information and a tool use count from the second NFC module via the established NFC link; determine if the surgical tool is usable based on the received tool usability information; and if the received tool usability information indicates that the surgical tool is unusable, trigger a tool identification error indicate a failure to initialize the surgical tool.

In some embodiments, wherein if the received tool usability information indicate s that the surgical tool is usable, the one or more processors are further configured to: check to determine if the surgical tool has been previously used in the surgical procedure; and if so: retrieve tool calibration data directly from a cache of the robotic surgical system and use the retrieved tool calibration data to initialize the surgical tool so that the surgical tool is ready for use in the surgical procedure.

In some embodiments, if it is determined that the surgical tool has not been used in the surgical procedure, the one or more processors are further configured to: decrement the received use count of the surgical tool and update the use count of the surgical tool in the second NFC module via the established NFC link.

In some embodiments, the first NFC module includes an NFC reader, and the second NFC module includes an NFC tag.

BRIEF DESCRIPTION OF THE DRAWINGS

The structure and operation of the present disclosure will be understood from a review of the following detailed description and the accompanying drawings in which like reference numerals refer to like parts and in which:

FIG. 4 shows a cross-sectional view of an exemplary tool drive of FIGS. 3A and 3B loaded with an exemplary surgical tool and an exemplary near-field communication (NFC) module disposed at the interface between the tool drive and the surgical tool in accordance with some embodiments described herein.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout this patent disclosure, the term "surgical procedure" generally refers to a complete operating room procedure performed on a patient; whereas the term "surgical session" generally refers to a segment of a given surgical procedure demarcated by at least one tool attachment event.

In light of the problems described in the background section, certain types of wireless connections became desirable communication options between the surgical tool and the surgical robot because these wireless connections do not require an open connection. These wireless connections can include, but are not limited to: Bluetooth connections, WI-FI connections, and certain radio-frequency identification (RFID) connections. However, Bluetooth connections and WI-FI connections require a dedicated power source. Unfortunately, putting such a power source inside the surgical tool to enable Bluetooth connections or WI-FI connections is not desirable. Near-field communication (NFC), as a form of RFID connections becomes an ideal choice because an NFC module can be electrically passive, while NFC field generated from a tool drive of the robot arm can provide power wirelessly to the NFC module inside the surgical tool and power up the NFC microcontroller inside the NFC module.

This patent disclosure provides various embodiments of using NFC to facilitate the transfer of data and power between a robotic surgical system and a surgical tool attached to the robotic surgical system. More specifically, NFC modules, such as an NFC tag and an NFC reader can be respectively embedded in the surgical tool and the surgical robot, wherein each NFC modules can further include a microcontroller and a memory. Using the NFC modules, an NFC communication link can be established between the surgical robot and the surgical tool, so that data and power can be transmitted from the NFC module embedded in the surgical robot to the NFC module embedded in the surgical tool. The NFC module in the surgical tool, once booted up will be ready to respond to the data request from the surgical robot through the established NFC communication link (or "NFC link" hereinafter).

Figure 1:
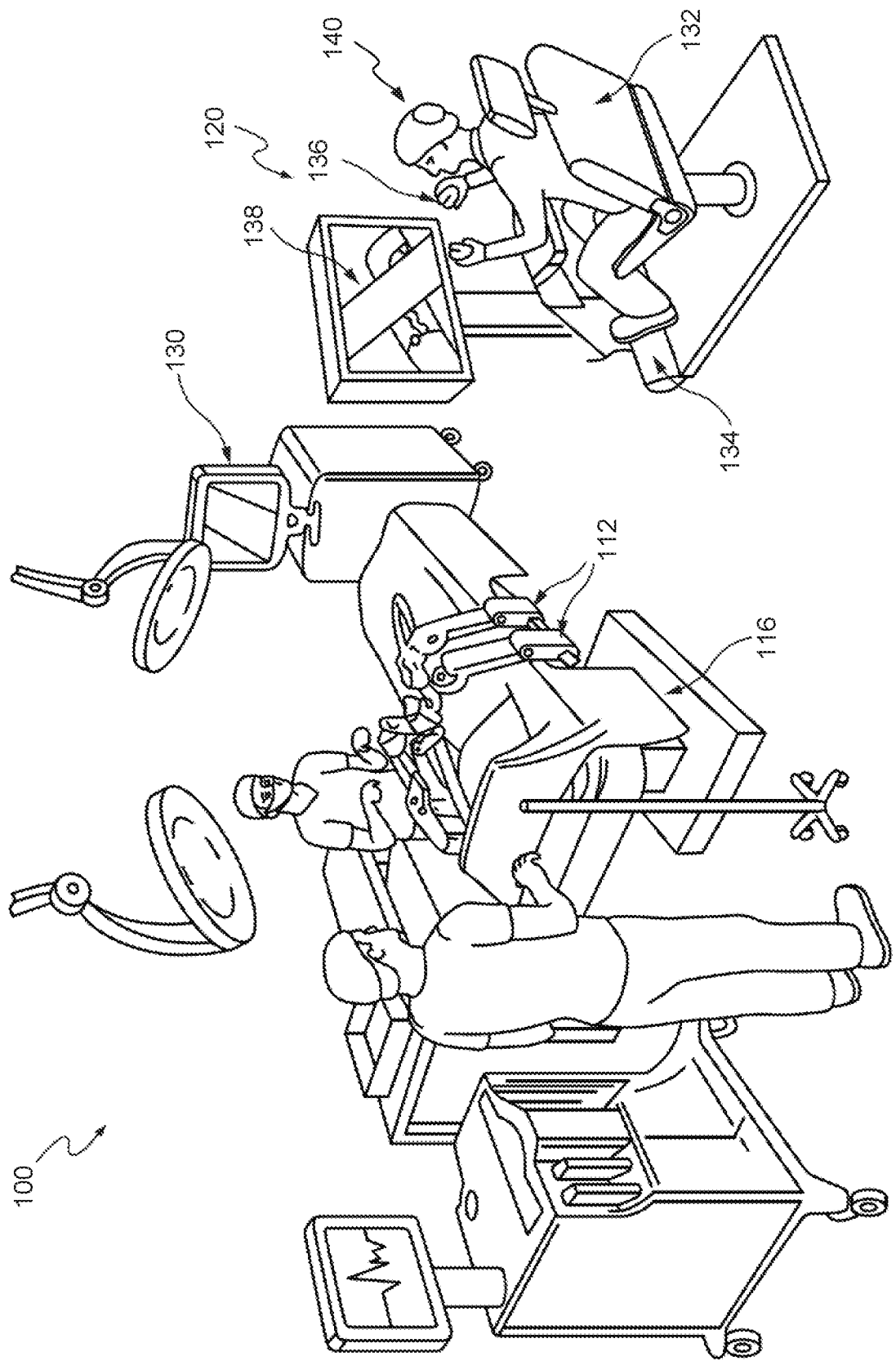
FIG. 1 shows a diagram illustrating an exemplary operating room environment with a robotic surgical system for implementing the disclosed NFC-based surgical tool/surgical robot communication in accordance with some embodiments described herein.

FIG. 1 shows a diagram illustrating an exemplary operating room environment with a robotic surgical system 100 for implementing the disclosed NFC-based surgical tool/surgical robot communication in accordance with some embodiments described herein. As shown in FIG. 1, robotic surgical system 100 comprises a surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., teleoperation). User console 120 may be located in the same operating room as robotic surgical system 100, as shown in FIG. 1. In other environments, user console 120 may be located in an adjacent or nearby room, or teleoperated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed or withdrawn configuration to facilitate access to the surgical site. Once the access is achieved, initial positioning and/or preparation of the robotic system may be performed. During the procedure, a surgeon in the user console 120 may use the foot-operated controls 134 and/or UIDs 136 to manipulate various surgical tools/end effectors and/or imaging systems to perform the surgery. Manual assistance may also be provided at the procedure table by sterile-gowned personnel, who may perform tasks including, but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures including, but not limited to, robotic surgical system 100 cleaning and/or sterilisation, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit them to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 2:
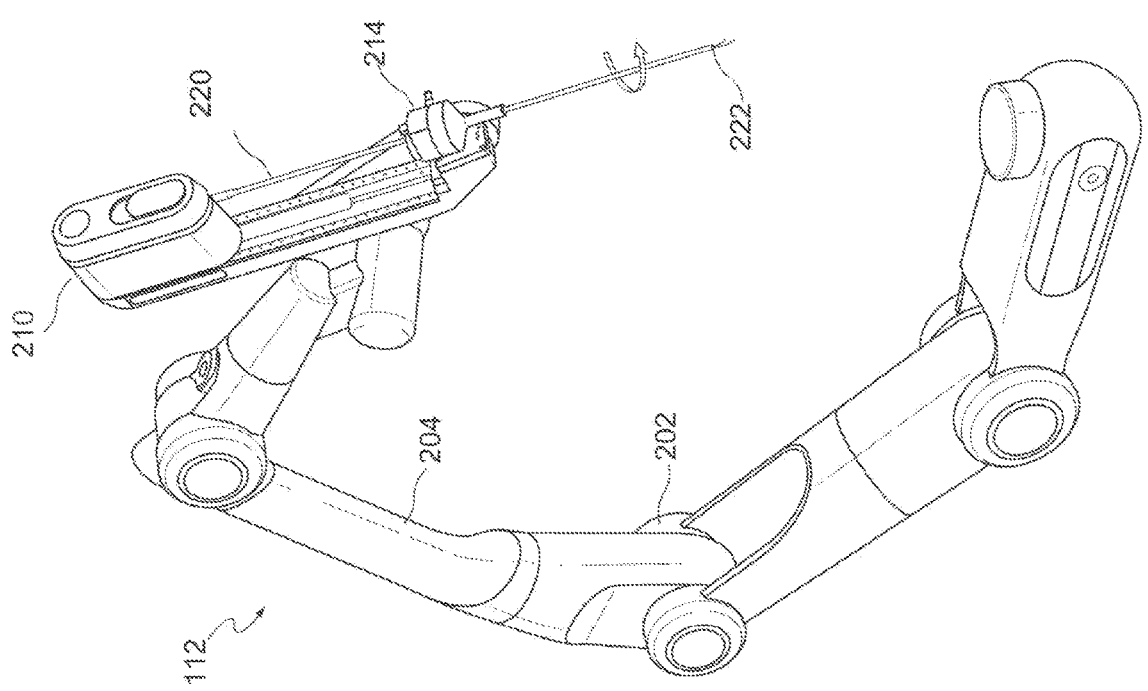
FIG. 2 shows a schematic diagram illustrating an exemplary design of a robotic arm of the robotic surgical system, which is loaded with a tool drive and a cannula that is further loaded with a robotic surgical tool, in accordance with some embodiments described herein.

FIG. 2 shows a schematic diagram illustrating an exemplary design of a robotic arm 112 of robotic surgical system 100, which is loaded with a tool drive 210 and a cannula 214 that is further loaded with a robotic surgical tool 220, in accordance with some embodiments described herein. As shown in FIG. 2, the exemplary surgical robotic arm 112 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 112. The tool drive 210 may include a cannula 214 coupled to its end to receive and guide a robotic surgical instrument 220 (e.g., endoscopes, staplers, etc.). This robotic surgical instrument 220 (also referred to as the "robotic surgical tool 220" or the "surgical tool 220" below) may include an end effector 222 at the distal end of the surgical tool 220. The plurality of the joint modules of the robotic arm 112 can be actuated to position and orient the tool drive 210, which actuates the end effector 222 of the robotic surgical tool 220 for robotic surgeries.

Figure 3A:
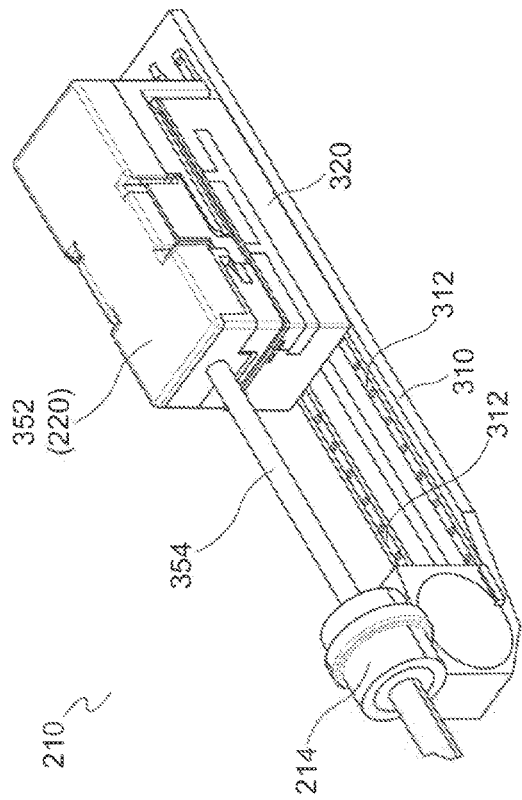
FIGS. 3A and 3B show schematic diagrams illustrating an exemplary tool drive with and without a loaded surgical tool, respectively, in accordance with some embodiments described herein.
Figure 3B:
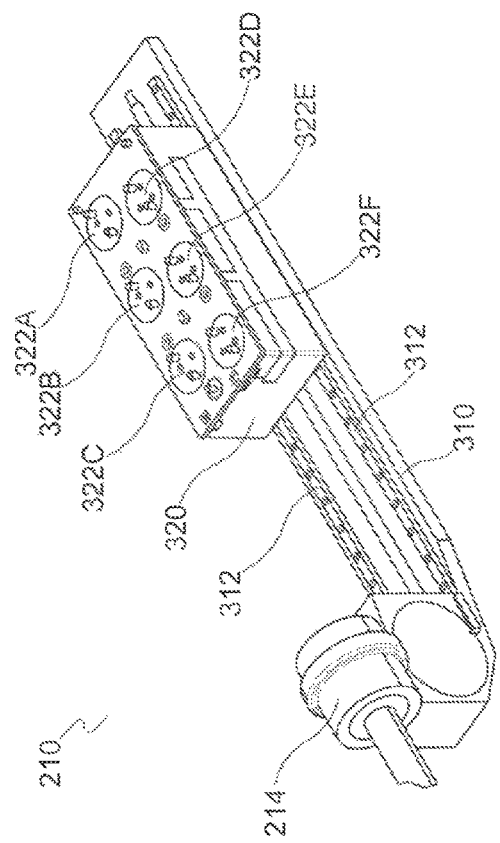

FIGS. 3A and 3B show schematic diagrams illustrating an exemplary tool drive 210 of FIG. 2 with and without a loaded surgical tool 220, respectively, in accordance with some embodiments described herein. As shown in both FIGS. 3A and 3B, in one variation, the exemplary tool drive 210 can include an elongated base (or "stage") 310 having longitudinal tracks 312 and a tool carriage 320, which is slidingly engaged with the longitudinal tracks 312. The stage 310 can be configured to couple to the distal end of a robotic arm such that articulation of the robotic arm positions and/or orients the tool drive 210 in space. Additionally, as shown in FIG. 3A, the tool carriage 320 can be configured to receive a tool base 352 of the surgical tool 220, which may also include a tool shaft 354 extending from the tool base 352 and through the cannula 214 of the tool drive 210, with the end effector 222 (not shown) of the surgical tool 220 disposed at the distal end of the surgical tool 220.

Additionally, the tool carriage 320 of the exemplary tool drive 210 can actuate a set of articulated movements of the end effector 222, such as through a cable system or wires manipulated and controlled by actuated drives (the terms "cable" and "wire" are used interchangeably throughout this patent disclosure). The tool carriage 320 can include different configurations of actuated drives. For example, the rotary axis drives can include a motor with a hollow rotor and a planetary gear transmission at least partially disposed within the hollow rotor. The plurality of rotary axis drives can be arranged in any suitable manner. For example, as shown in FIG. 3B, the exemplary tool carriage 320 can include six rotary drives 322A-322F arranged in two rows, extending longitudinally along the base 310 that are slightly staggered to reduce width of the carriage and increase the compact nature of the tool drive 210. As clearly shown in FIG. 3B, rotary drives 322A, 322B, and 322C can be generally arranged in a first row, while rotary drives 322D, 322E, and 322F can be generally arranged in a second row that is slightly longitudinally offset from the first row.

FIG. 4 shows a cross-sectional view of an exemplary tool drive 210 of FIGS. 3A and 3B loaded with an exemplary surgical tool 220 and an exemplary near-field communication (NFC) mechanism 400 disposed at the interface between tool drive 210 and surgical tool 220 in accordance with some embodiments described herein. Note that in FIG. 4, both the stage 310 of tool drive 210 and tool shaft 354 of surgical tool 220 are only partially shown, while the end effector of surgical tool 220 is not shown.

As can be seen in FIG. 4, the disclosed NFC mechanism 400 includes an NFC tag 402 disposed inside tool base 352 of surgical tool 220, and more specifically in the vicinity of the bottom surface of tool base 352 which is received by tool carriage 320 of tool drive 210. NFC mechanism 400 also includes NFC reader 412 disposed inside tool carriage 320 of tool drive 210, and more specifically in the vicinity of the top surface of tool carriage 320 which receives tool carriage 320 of surgical tool 220. Notably, the disclosed NFC mechanism 400 can be separately implemented on tool drive 210 of robotic surgical system 100 (i.e., NFC reader 412), and each specific surgical tool 220 (i.e., NFC tag 402). As such, NFC mechanism 400 is formed and enabled through the attachment of each specific surgical tool 220 onto tool drive 210 of robotic surgical system 100.

As shown in FIG. 4, NFC tag 402 can include an integrated circuit (IC) chip/microcontroller 404 which further includes a memory (not shown) for storing tool-specific data, and other circuits such as a memory controller and a controller unit for controlling antenna frequencies and data transmission. NFC tag 402 also includes one or more antennas 406, such as a loop antenna for receiving instructions from NFC reader 412 by way of magnetic induction and transmitting data retrieved from the memory to NFC reader 412 in response. In some embodiments, NFC tag 402 does not have to include or be coupled to a power source. Instead, NFC tag 402 is a passive device driven by a wireless power, e.g., a magnetic field generated by NFC reader 412. General speaking, NFC tag 402 can be implemented with any type of passive NFC tags now known or later developed.

As shown in FIG. 4, NFC reader 412 can include an IC chip/microcontroller 414 which further includes an NFC reader IC for generating instructions and an antenna control unit for controlling frequencies and signal transmission. NFC reader 412 also includes one or more antennas 416, such as a loop antenna for transmitting the generated instructions to NFC tag 402 as magnetic fields and receiving tool-specific data from NFC tag 402 in response. Although not shown, NFC reader 412 is coupled to a power source which provides power to IC chip/microcontroller 414 and the one or more antennas 416. Moreover, NFC reader 412 may be coupled to additional circuitries such as a microcontroller. Note that NFC reader 412 can be implemented with any type of NFC readers now known or later developed.

Various embodiments of this patent disclosure use near-field communication to facilitate the transfer of data between robotic surgical system 100 and surgical tool 220, and the transfer of data and power to NFC tag 402 of NFC mechanism 400 including the microcontroller 404 within surgical tool 220. NFC tag 402 within surgical tool 220, once booted up is ready to respond to the data request from robotic surgical system 100 through an NFC link established between NFC tag 402 and NFC reader 412. In some embodiments, the NFC link between NFC tag 402 within tool 220 and NFC reader 412 within tool drive 210 of robotic surgical system 100 (also referred to as "robotic system 100" or "surgical robot 100" hereinafter) is only established after the physical tool attachment is complete.

Once the NFC link is established, data communication between robotic surgical system 100 and surgical tool 220 via the NFC link facilitates the authentication of tool 220 and the establishment of a secure data exchange mechanism between robotic surgical system 100 and surgical tool 220 through a disclosed tool authentication sequence. After tool 220 has been authenticated and secure data exchange has been established, encrypted data exchange between robotic surgical system 100 and surgical tool 220 via the NFC link further facilitates the identification and initialization of tool 220. However, from the initial attachment of tool 220 onto the tool drive 210 until the initialization of tool 220 by robotic system 100, various types of errors can occur at different stages of setting up tool 220, which would lead to the removal of tool 220. The description below provides detailed embodiments of the newly-attached tool 220 setup procedure based on the disclosed NFC mechanism and link and various failure modes associated with the tool 220 setup procedure. The description below can be better understood in conjunction with both FIG. 4 and a state machine diagram 500 of FIG. 5, which comprises a set of states/events from initial tool attachment until successful tool initialization and a set of error events which causes a given state to transition toward tool removal state in accordance with some embodiments described herein.

Figure 5:
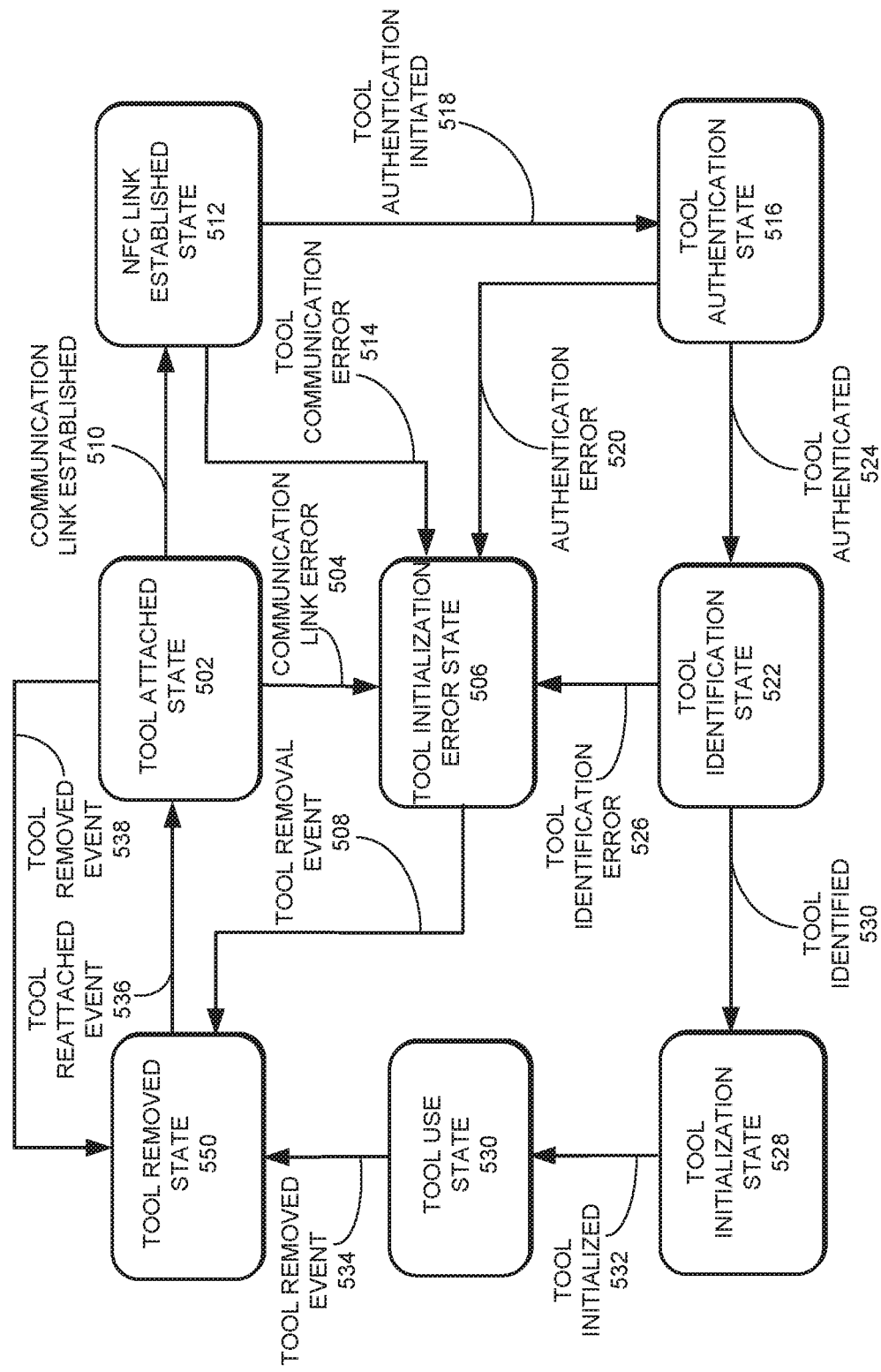
FIG. 5 illustrates a state machine diagram which comprises a set of states/events from initial tool attachment until successful tool initialization and a set of error events which causes a given state to transition toward tool removal state in accordance with some embodiments described herein.

As can be seen in FIG. 5, immediately after attaching tool 220 onto tool drive 210 of robotic system 100, state machine diagram 500 enters "tool attached state" 502. At this moment, NFC tag 402 remains disabled even if tool drive 210 is powered on because no power is initially applied to NFC reader 412. At the same time, the initial tool attachment can be detected by one or multiple sensors installed on tool drive 210 and robotic system 100, e.g., when a magnet embedded in tool 220 is sensed by a magnetic field sensor embedded in tool drive 210. When the tool attachment is detected, robotic system 100 can initiate the establishment of an NFC link/channel between NFC tag 402 and NFC reader 412. For example, robotic system 100 can first cause tool drive 210 to supply power to NFC reader 412, which then transmits wireless power to NFC tag 402 within tool 220 to allow NFC tag 402 to boot up. This step may serve as an initiation request of subsequent NFC link/channel establishment. Once the microcontroller 404 within NFC tag 402 boots up, microcontroller 404 is configured to continue establishing an NFC link/channel with NFC reader 412. In some embodiments however, NFC reader 412 can send a dedicated link initiation request to NFC tag 402 separated from the transmitting the wireless power to NFC tag 402. Note that, because an NFC link/channel between NFC tag 402 and NFC reader 412 is to serve as a communication channel between robotic system 100 and tool 220, an NFC link/channel established or being established between NFC tag 402 and NFC reader 412 is also referred to as an NFC link/channel "between robotic system 100 and tool 220" below.

While we have described initiating an NFC link after the full attachment of surgical tool 220 onto tool drive 210 above, the communication between NFC tag 402 in surgical tool 220 and NFC reader 412 in tool drive 210 may begin when NFC tag 402 is being brought into the vicinity of NFC reader 412 in the process of attaching surgical tool 220 onto tool drive 210. For example, NFC tag 402 and NFC reader 412 may be designed such that the communication between NFC tag 402 and NFC reader 412 begins when NFC tag 402 is brought within a maximum workable distance (e.g., a few millimeters) to the NFC reader 412 and tool drive 210 (but not working if beyond this distance). Hence, even before surgical tool 220 is fully attached to tool drive 210, robotic system 100 may begin setting up an NFC link with NFC tag 402 of tool 220. As such, an NFC link between tool 220 and robotic system 100 may be established during the tool attachment and before tool 220 is fully attached onto robotic arm 112.

Note that the attempt to establish an NFC link between robotic system 100 and tool 220 through NFC mechanism 400 can fail in multiple ways, even when both NFC tag 402 and NFC reader 412 are properly powered on and enabled (i.e., after NFC tag 402 receives wireless power from NFC reader 412 and subsequently boots up). More specifically, when the powered-up NFC tag 402 attempts to establish an NFC link with NFC reader 412, but for some reason the NFC link cannot be established, then a communication link error 504 is triggered which is generally generated by robotic system 100. Note that this communication link error is generally associated with a physical layer (i.e., the lowest layer) error while transmitting raw bits from NFC tag 402 to NFC reader 412. For example, this communication link error can occur when a wrong surgical tool is attached to the tool drive 210. As shown in the state machine diagram of FIG. 5, communication link error 504 causes tool attached state 502 to transition to tool initialization error state 506, which then leads to tool removed state 550 through a tool removal event 508 that removes the attached tool 220 from tool drive 210. Note that communication link error 504 can be viewed as the first type of tool initialization error during the process of initializing the newly-attached tool 220.

However, if robotic system 100 receives a proper response from NFC tag 402 in response to the initial link initiation request, robotic system 100 determines that the NFC link with NFC tag 402 and tool 220 has been established. In state machine diagram of FIG. 5, this scenario corresponds to the transition from tool attached state 502 to NFC link established state 512 through the event of communication link established 510. Next, robotic system 100 can initiate a tool authentication sequence to set up the data exchange between robotic system 100 and tool 220. Generally speaking, the disclosed tool authentication sequence is used to establish mutual trust between robotic system 100 and tool 220. In some embodiments, the disclosed tool authentication sequence involves two sequential procedures: (1) a certificate validation procedure wherein robotic system 100 and tool 220 exchange certificates with each other and validate each other's authenticity; and (2) session key procedure wherein robotic system 100 and tool 220 establish a symmetric key for secure data exchange. Similarly, both the disclosed certificate validation procedure and the session key procedure can be executed between robotic system 100 and NFC tag 402 of tool 220 via the established NFC link.

In some embodiments, the certificate validation procedure of the disclosed tool authentication sequence can begin when robotic system 100 sends a first authentication data sequence including the robot certificate to tool 220, which also serves as a request for the tool certificate of tool 220. However, the tool authentication sequence between robotic system 100 and NFC tag 402 can fail to proceed at the beginning of the certificate validation procedure, subsequently causing a tool communication error 514. In particular, after robotic system 100 has sent the first authentication data sequence, if robotic system 100 fails to receive any response from tool 220 after a predetermined time period has passed, a timeout event occurs and a tool communication error 514 is triggered.

Note that tool communication error 514 is generally associated with the data link layer error. For example, tool communication error 514 can be caused by data corruption/lost during transmission. Moreover, this tool communication error can be caused by data error in the protocol level, e.g., if tool 220 fails to interpret the received authentication data sequence as something meaningful. As shown in the state machine diagram of FIG. 5, tool communication error 514 causes a transition from NFC link established state 512 to tool initialization error state 506, which then leads to tool removed state 550 through a tool removal event 508 that removes the attached tool 220 from tool drive 210. Note that tool communication error 514 can be viewed as the second type of tool initialization error (in contrast to the first type of tool initialization error associated with communication link error 504) during the process of initializing the newly-attached tool 220.

However, if the initial step of the tool authentication process is able to proceed, the actual certificate validation procedure can then be carried out. This is shown in FIG. 5 as the state machine diagram 500 transitions from NFC link established state 512 to tool authentication state 516 following the event of tool authentication initiated 518. In some embodiments, the actual certificate validation procedure can be carried out in accordance with a TLS-handshake procedure. More specifically, robotic system 100 can provide a robot certificate to tool 220 via the established NFC communication link. Moreover, robotic system 100 can provide the robot certificate encrypted with a public key of robotic system 100. Upon receiving the encrypted robot certificate, tool 220 will first decrypt the encrypted robot certificate with a matching private key of tool 220. Next, tool 220 will compare the received robot certificate with a robot ID stored in its memory to validate the robot certificate. For example, the robot ID can be stored within the memory of NFC tag 402. If the received robot certificate matches the robot ID, tool 220 validates the authenticity of robotic system 100, and the trust between robotic system 100 and tool 220 is partially established.

Note that in the above-described certificate validation procedure taking placing on tool 220, if tool 220 fails to decrypt the public key of robotic system 100 with a matching private key or if the received robot certificate does not match a stored robot ID, the tool authentication sequence fails and an authentication error 520 is triggered. As shown in the state machine diagram of FIG. 5, authentication error 520 causes a transition from tool authentication state 516 to tool initialization error state 506, which then leads to tool removed state 550 through a tool removal event 508 that removes the attached tool 220 from tool drive 210, thereby terminating the NFC link. Note that tool authentication error 520 can be viewed as the third type of tool initialization error (in contrast to the above-described first type and the second type of tool initialization errors) during the process of initializing the newly-attached tool 220.

In various embodiments, the received robot certificate also serves as a challenge by robotic system 100 to tool 220. Hence, in the next step of the certificate validation procedure, tool 220 sends a tool certificate back to robot system 100 via the established NFC link. Moreover, tool 220 can provide the tool certificate encrypted with a public key of tool 220. Similarly, upon receiving the encrypted tool certificate, robotic system 100 will first decrypt the encrypted tool certificate with a matching private key of robotic system 100. Next, robotic system 100 will validate the received tool certificate to verify that tool 220 is a valid tool for robotic system 100. If the tool certificate is successfully validated, robotic system 100 and tool 220 have successfully authenticated each other, and the trust between robotic system 100 and tool 220 is fully established.

However, if robotic system 100 fails to decrypt the public key of tool 220 with a matching private key or if the authenticity of the received tool certificate cannot be validated, the tool authentication sequence fails and authentication error 520 is triggered. As mentioned above, tool authentication error 520 causes a transition from tool authentication state 516 to tool initialization error state 506, which subsequently causes the attached tool 220 to be removed from tool drive 210, thereby terminating the NFC link.

Note that the above-described bi-directional certificate validation procedure is an asymmetric key procedure, which is generally more computationally expensive than a symmetric key procedure that uses a single symmetric key. Because asymmetric communication is more computationally expensive, in some embodiments, a symmetric/session key will be used during the subsequent data communication. More specifically, this symmetric key will be used by both robotic system 100 and tool 220 during data exchange, i.e., for both encryption and decryption on both ends, which can be much faster than an asymmetric key procedure. Hence, in the session key procedure of the disclosed tool authentication sequence, a session key has to be set up between robotic system 100 and tool 220.

In some embodiments, the session key can be set up through a key challenge. In a particular embodiment, robotic system 100 is configured to generate a crypto challenge, e.g., by way of a random number and send the random number unencrypted to tool 220. Meanwhile, robotic system 100 also generates a symmetric key (also referred to as the "session key"). Next, tool 220 receives the crypto challenge, e.g., the random number and subsequently encrypts the received challenge with a session/symmetric key the tool has generated on its end. Tool 220 then sends the encrypted crypto challenge, e.g., the encrypted random number back to robotic system 100.

Once receiving the encrypted crypto-challenge from tool 220, robotic system 100 attempts to decrypt the encrypted crypto challenge from the tool with its own session/symmetric key. If the session key generated by robotic system 100 does not match the session key generated by tool 220, the tool authentication sequence fails and authentication error 520 is triggered. Similarly, authentication error 520 causes a transition from tool authentication state 516 to tool initialization error state 506, which subsequently causes the attached tool 220 to be removed from tool drive 210. However, if the session key generated by robotic system 100 matches the session key generated by tool 220, robotic system 100 will get back the same crypto challenge, e.g., the same random number it has generated and the crypto challenge is successfully resolved.

Once the symmetric key is established between robotic system 100 and tool 220, the tool authentication sequence is complete, and tool 220 is successfully initialized. This is shown in FIG. 5 as the state machine diagram 500 transitions from tool authentication state 516 to tool identification state 522 following the event of tool authenticated 524. In some embodiments, the entire tool initialization and authentication process can take a few seconds to complete. Next, data exchange between robotic system 100 and tool 220 can begin by using the established symmetric key so that data being exchange can be encrypted and communication is secure. More specifically, data to be transmitted between robotic system 100 and tool 220 can be first encrypted with the symmetric key and the encrypted data are then transmitted. Moreover, the symmetric key can be used to decrypt the data when the encrypted data are received. As mentioned above, because the same symmetric key is used by both robotic system 100 and tool 220 for both encryption and decryption, using the symmetric key for data exchange is faster than using asymmetric keys. Note that this session/symmetric key is established in real time and therefore can be different for different tool authentication sequences associate with different tool attachment events.

After establishing the secure data communication link between robotic system 100 and tool 220, robotic system 100 can then request tool identification info (or "tool info") by sending a tool info request via the established NFC link. Specifically, robotic system 100 can transmit the tool info request from NFC reader 412 to NFC tag 402 via the established NFC link. In some embodiments, the requested tool info can include, but is not limited to a tool ID, a tool type, a product code, tool generation and version numbers, a use count, and one or more usability flags. Upon receiving the tool info request, microcontroller 404 within NFC tag 402 is configured to retrieve the requested tool info from a memory, such as a memory within microcontroller 404, encrypt the retrieved data with the established symmetric key and subsequently transmit the encrypted tool info to robotic system 100 via the established NFC link. In some other embodiments however, tool 220 may transmit the tool info back to robotic system 100 unencrypted. Next, upon receiving the encrypted tool info at robotic system 100, robotic system 100 is configured to decrypt the encrypted tool info with the same symmetric key to get back the requested tool data, parse the tool data to determine the tool ID, the tool type, the generation and version numbers, the use count, and the one or more usability flags, among others.

However, at the point, a tool identification error 526 can occur based on the tool info received from tool 220. Generally speaking, a tool identification error 526 occurs when the received tool info indicates that tool 220 is not usable due to one of a number of predetermined reasons. For example, the received use count can indicate that the tool is not usable because the tool has exceeded the maximum use count/limit which is part of the tool specification. As another example, the received tool type can indicate that tool 220 is not usable because the specific tool type is not compatible or supported by robotic system 100. As still another example, the received version number can indicate that tool 220 is not usable because the data version is not compatible or supported by robotic system 100. Note that the received tool data can indicate that tool 220 is not usable as a result of the tool is marked as unusable for other reasons specified by the one or more usability flags. This is shown in FIG. 5 as the state machine diagram 500 transitions from tool identification state 522 to tool initialization error state 506 following the event of tool identification error 526, which subsequently causes the attached tool 220 to be removed from tool drive 210.

However, if tool 220 is successfully identified/recognized by robotic system 100 without any tool identification error, tool 220 is successfully identified. This is shown in FIG. 5 as the state machine diagram 500 transitions from tool identification state 522 to tool initialization state 528 following the event of tool identified 530. Next, robotic system 100 can check to determine if tool 220 has been previously used (i.e., attached on robotic system 100) during the same surgical procedure. For example, robotic system 100 can search a log file which keeps records of all the surgical tools which have been used in the same surgical procedure before the current tool attachment.

If robotic system 100 determines that tool 220 has been previously used/attached in the same surgical procedure, certain tool data, such as tool calibration data and a set of tool specific parameters should have been cached on robotic system 100, and therefore do not need to be requested again from tool 220. Instead, these cached tool data can be retrieved directly from a cache of robotic system 100. Subsequently, robotic system can use the retrieved tool data including the tool calibration data to initialize, e.g., homing the newly-attached surgical tool so that surgical tool is ready for use in the current surgical session. This is shown in FIG. 5 as the state machine diagram 500 transitions from tool initialization state 528 to tool use state 530 following the event of tool initialized 532. Note that in this scenario, robotic system 100 does not deduct the use count for tool 220 for the current attachment. By the same token, for a given surgical procedure/session, tool 220 use count can be fixed to one time or 1 (i.e., the remaining use count is only deducted by 1), no matter how many times tool 220 was detached and reattached (i.e., being used multiple times) during the same surgical procedure.

Further referring to FIG. 5, note that after some proper use in tool use state 530 during the surgical session, tool 220 can be removed from robotic system 100 which causes the state machine diagram 500 to transition from tool use state 530 to tool removed state 550 following tool removal event 534. However, after the removal, tool 220 can be reattached onto robotic system 100 during the same surgical procedure, which causes state machine diagram 500 to transition from tool removed state 550 to tool attached state 502 following tool reattached event 536. Note that FIG. 5 also shows that a newly-attached tool can be removed without going through the various tool setup procedures, so that state machine diagram 500 returns to tool removed state 550 from tool attached state 502 following tool removed event 538.

However, if robotic system 100 determines that tool 220 has not been previously attached during the same surgical procedure, then robotic system 100 determines that a new tool is attached and identified. At this point, robotic system 100 can be configured to decrement the use count of the tool and request tool calibration data and a set of tool specific parameters directly from tool 220. More specifically, robotic system 100 is configured to send the request for tool calibration data, a set of tool specific parameters to tool 220 via the established NFC link. As an example, each surgical tool can have a different geometry which is represented by a parameter called "UIDN," and this geometry parameter can be part of the set of tool specific parameters to be sent to robotic system 100.

Similar to the tool info request, robotic system 100 can transmit the tool data request from NFC reader 412 to NFC tag 402 via the established NFC link. Upon receiving the data request, microcontroller 404 within NFC tag 402 is configured to retrieve the requested tool data from a memory, such as a memory within microcontroller 404, encrypt the retrieved data with the established symmetric key and subsequently transmit the encrypted tool data to robotic system 100 via the established NFC link. In some embodiments, robotic system 100 can be configured to decrement the use count of tool 220 only after receiving the requested tool data from tool 220. The received tool data including the tool calibration data and the tool specific parameters can then be stored in a cache on robotic system 100 for future retrieval.

Using the received tool data including the tool calibration data, the control algorithm of robotic system 100 can initialize the newly-attached tool 220 to be ready for use in the surgical session. This is also shown in FIG. 5 as the state machine diagram 500 transitions from tool initialization state 528 to tool use state 530 following the event of tool initialized 532. The control algorithm of robotic system 100 can also use the received tool specific parameters to control the tool during the given surgical session. In some embodiments, after receiving the tool data, the established NFC link can be disabled, because no data needs to be exchanged between robotic system 100 and tool 220 during the subsequent surgical session. However, as will be discussed below, the NFC link between robotic system 100 and tool 220 may be reestablished during or at the end of the given surgical session so that certain data related to tool operation, certain summary of the tool usage, or certain tool failure-related data can be written into a tool log maintained on tool 220. As can be appreciated from the discussion above, the disclosed NFC links/channels are primarily used for authenticating and initializing newly-attached surgical tools, and for transmitting tool-specific info and data from a newly-connected surgical tool to robotic system 100.

Note that when tool 220 is later removed from robotic system 100 after some normal use but is reattached during the same surgical procedure, robotic system 100 and tool 220 will go through the above-described tool initiation process again. During the new initiation process, the NFC link will be reestablished, a new symmetric/session key will be produced during the tool authentication process and used for the new surgical session/phase. As mentioned above, during the new tool initiation process, robotic system 100 can obtain the tool calibration data and certain tool-specific parameters directly from the cache. Moreover, robotic system 100 does not decrement the remaining tool use count during the new initiation process.

In some embodiments, tool 220 can maintain a tool log on microcontroller 404, e.g., within a memory of microcontroller 404. In some embodiment, this tool log can be used to record certain data related to tool operation during the surgical session after the tool has been initiated. For example, when tool 220 is attached to robotic system 100 for the first time for a given surgical procedure, a session ID can be generated and stored into the tool log. As another example, if for some reason tool 220 fails during the surgical procedure, tool failure-related data, such as an error code can be stored into the tool log. Hence, tool manufacture can examine the tool log later on to determine the failure mode based on the error code stored in the tool log.

Additional tool-related info that can be stored in the tool log can include certain summary of the tool usage at the end of the surgical procedure, such as the duration of the tool attachment. Such usage summary can be unique to a specific tool type, e.g., for a stapler, the usage summary can include how many times the stapler has been fired during a given surgical session and during the entire surgical procedure. In some embodiments, the remaining use count of tool 220 can be stored in the tool log and updated as necessary based on the above-described use count update options. Note that the tool-related info that can be stored in the tool log is not limited to the end of the session summary, but can also include certain in-session tool information.

Note that because the NFC link is preferably disabled during the surgical session involving tool 220, updating the tool log on NFC tag 402 can take place at the end of the surgical session. For example, prior to detaching tool 220, user of robotic system 100 may trigger NFC link to be re-established through a user interface, and wait for the tool data log to complete before removing tool 220. In some embodiments, the tool log may be periodically updated during a surgical session for tool 220. In these embodiments, the NFC link may be periodically and automatically re-established during the surgical session to allow the tool log to be updated. The NFC link can also be automatically disabled after each in-session tool log update.

Figure 6:
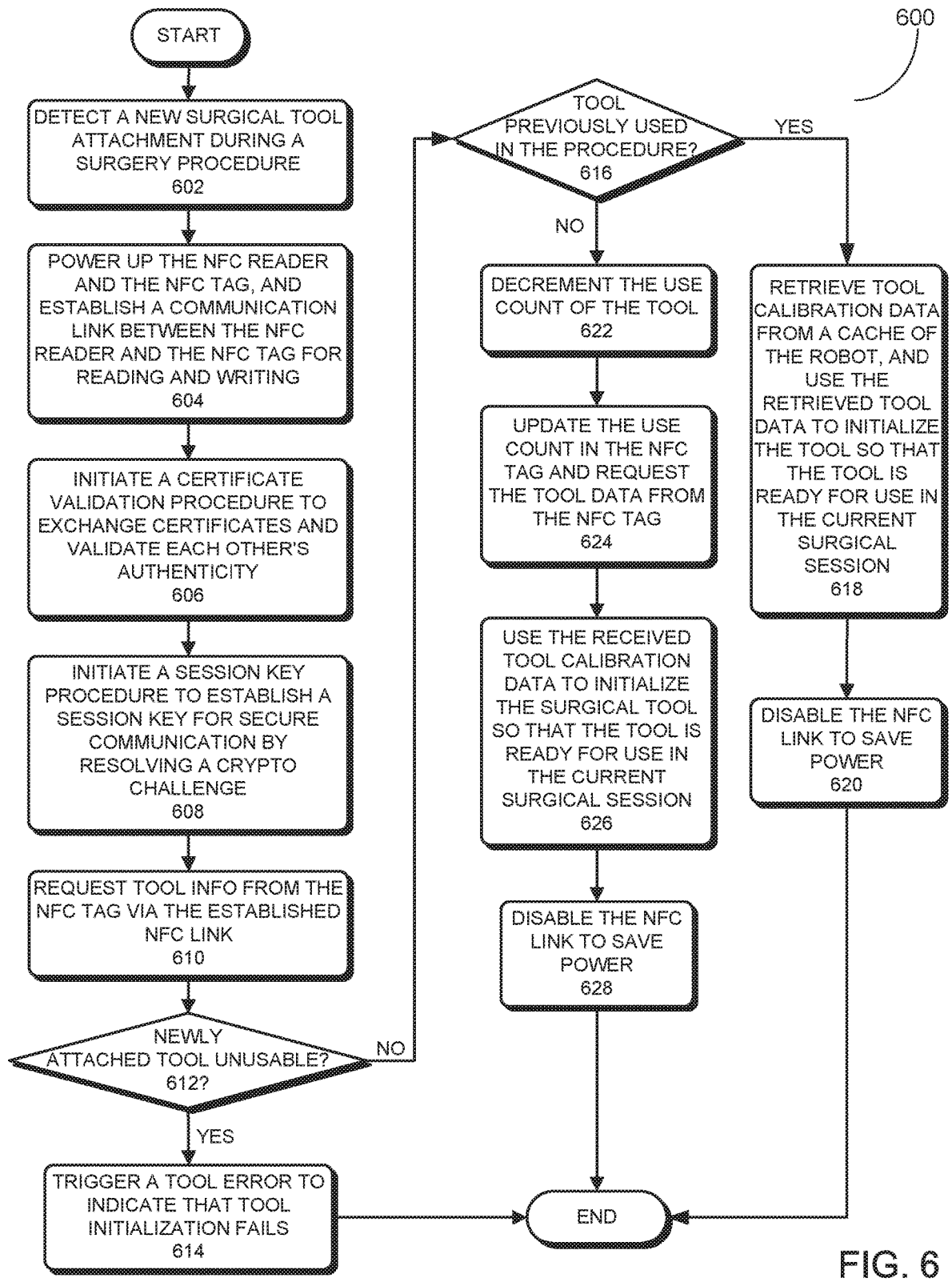
FIG. 6 presents a flowchart illustrating an exemplary process for managing a newly-attached surgical tool on a robotic system during a surgical procedure in accordance with some embodiments described herein.

FIG. 6 presents a flowchart illustrating an exemplary process 600 for managing a newly-attached surgical tool 220 on robotic system 100 during a surgical procedure in accordance with some embodiments described herein. In one or more embodiments, one or more of the steps in FIG. 6 may be omitted, repeated, and/or performed in a different order. Accordingly, the specific arrangement of steps shown in FIG. 6 should not be construed as limiting the scope of the technique. In the discussion below, robotic system 100 is simply referred to as "surgical robot" and the newly-attached surgical tool is simply referred to as "surgical tool."

Process 600 may begin when the surgical robot detects a new surgical tool attachment during a surgery procedure (step 602). In some embodiments, process 600 can begin when the surgical robot detects that the surgical tool is brought into the proximity of the robotic arm/tool drive before the surgical tool is fully attached onto the robotic arm/tool drive, e.g., when the surgical robot senses a magnetic field in the surgical tool. Next, the surgical robot powers up an NFC reader embedded in the tool drive, which in turn powers up an NFC tag embedded in the surgical tool, and establishes a communication link between the NFC reader and the NFC tag for reading and writing (step 604). In a particular embodiment, the NFC tag in the surgical tool is a passive device which only operable after receiving wireless power from the NFC reader. Recall that the attempt to establish a communication link between the NFC reader and the NFC tag can fail due to the above-described reasons which lead to the above-described communication link error 504. While step 604 assumes that the NFC link is successfully established between the NFC reader and the NFC tag, the alternatives to this scenario have been discussed above and in conjunction with the state machine diagram 500 of FIG. 5.

Next, the surgical robot initiates a certificate validation procedure wherein the surgical robot and the surgical tool exchange certificates with each other and validate each other's authenticity (step 606). As described above, the disclosed certificate validation procedure can include that: (1) the surgical robot transmits a robot certificate to the surgical tool encrypted with a public key of the surgical robot; (2) the surgical tool decrypts the received encrypted robot certificate with a matching private key and validate the authenticity of the received robot certificate; (3) in response to the certificate challenge, the surgical tool transmits a tool certificate to the surgical robot encrypted with a public key of the surgical tool; (4) the surgical robot decrypts the received encrypted tool certificate with a matching private key and validate the authenticity of the received tool certificate. Recall that the attempt to validate each other's authenticity between the surgical robot and the surgical tool can fail in a number of ways due to the above-described reasons, which can lead to the above-described tool communication error 514 or tool authentication error 518. While step 606 assumes that the surgical robot and the surgical tool successfully validate each other's authenticity and establish mutual trust, the alternatives to this scenario have been describe above and in conjunction with the state machine diagram 500 of FIG. 5.

Next in process 600, the surgical robot initiates a session key procedure wherein the surgical robot and the surgical tool establish a session key for secure communication by resolving a crypto challenge generated by the surgical robot (step 608). As described above, this session key procedure can include that: (1) the surgical robot generates a crypto challenge, such as a random number, and sends the crypto challenge unencrypted to the surgical tool; meanwhile generates a session/symmetric key; (2) the surgical tool encrypts the received crypto challenge with a session/symmetric key the surgical tool has generated on its end and sends the encrypted crypto challenge back to the surgical robot; (3) the surgical robot attempts to decrypt the received encrypted crypto challenge with its own session/symmetric key; (4a) if the decrypted crypto challenge does not match the original crypto challenge, the tool authentication sequence fails and a tool authentication error is triggered; or (4b) if the decrypted crypto challenge matches the original crypto challenge, the tool authentication sequence is complete, and a mutual session/symmetric key is established between the surgical robot and the surgical tool for encrypting data exchange between the surgical robot and the surgical tool. While step 608 assumes that the surgical robot and the surgical tool successfully establish the session/symmetric key, the alternative to this scenario has been described above and in conjunction with the state machine diagram 500 of FIG. 5.

Next in process 600, the surgical robot can request tool information including tool ID, tool type, product code, tool generation and version numbers, use count, and one or more usability flags from the NFC tag via the established NFC link (step 610). As described above, NFC tag can encrypt the tool information with the established symmetric key before transmitting the encrypted tool information to the surgical robot via the established NFC link. Next, based on the received tool information, the surgical robot determines if the newly-attached surgical tool is unusable (step 612). For example, the received use count can indicate that the surgical tool is unusable because the tool has exceeded the maximum use count/limit, or the received tool type can indicate that surgical tool is unusable because the specific tool type is not compatible or supported by the surgical robot, or the received version number can indicate that the surgical tool is unusable because the data version is not compatible or supported by the surgical robot, or the received usability flags indicate that tool is unusable as a result of other reasons specified by the usability flags. If the surgical robot determines that the newly-attached surgical tool is unusable, a tool identification error is triggered and tool initialization fails (step 614).

Otherwise, if the surgical tool is successfully identified by the surgical robot without any tool identification error, the surgical robot then checks to determine if the surgical tool has been previously used (i.e., attached on the surgical robot) during the same surgical procedure (step 616). If so, the surgical robot retrieves tool calibration data and tool specific parameters directly from a cache of the surgical robot, and uses the retrieved tool data to initialize the newly-attached surgical tool, e.g., homing the newly-attached tool so that the surgical tool is ready for use in the current surgical session (step 618). At this point, the established NFC link can be disabled during the subsequent surgical session to save power (step 620). However, the NFC link can also be reestablished periodically during the surgical session so that certain tool use data associated with the surgical session can be periodically written into a data log in the NFC tag via the reestablished NFC link.

However, if the surgical robot determines that the surgical tool has not been previously attached during the same surgical procedure, then the surgical robot decrements the use count of the surgical tool (step 622). Next, surgical robot updates the use count in the NFC tag via the established NFC link and also requests tool calibration data and tool specific parameters from the NFC tag (step 624). After receiving the tool calibration data and tool specific parameters from the NFC tag via the established NFC link, the surgical robot uses the received tool data to initialize the newly-attached surgical tool so that the surgical tool is ready for use in the current surgical session (step 626). Similarly, at this point, the established NFC link can be disabled during the subsequent surgical session to save power (step 628). However, the NFC link can also be reestablished periodically during the surgical session so that certain tool use data associated with the surgical session can be periodically written into a data log in the NFC tag via the reestablished NFC link.

Figure 7:
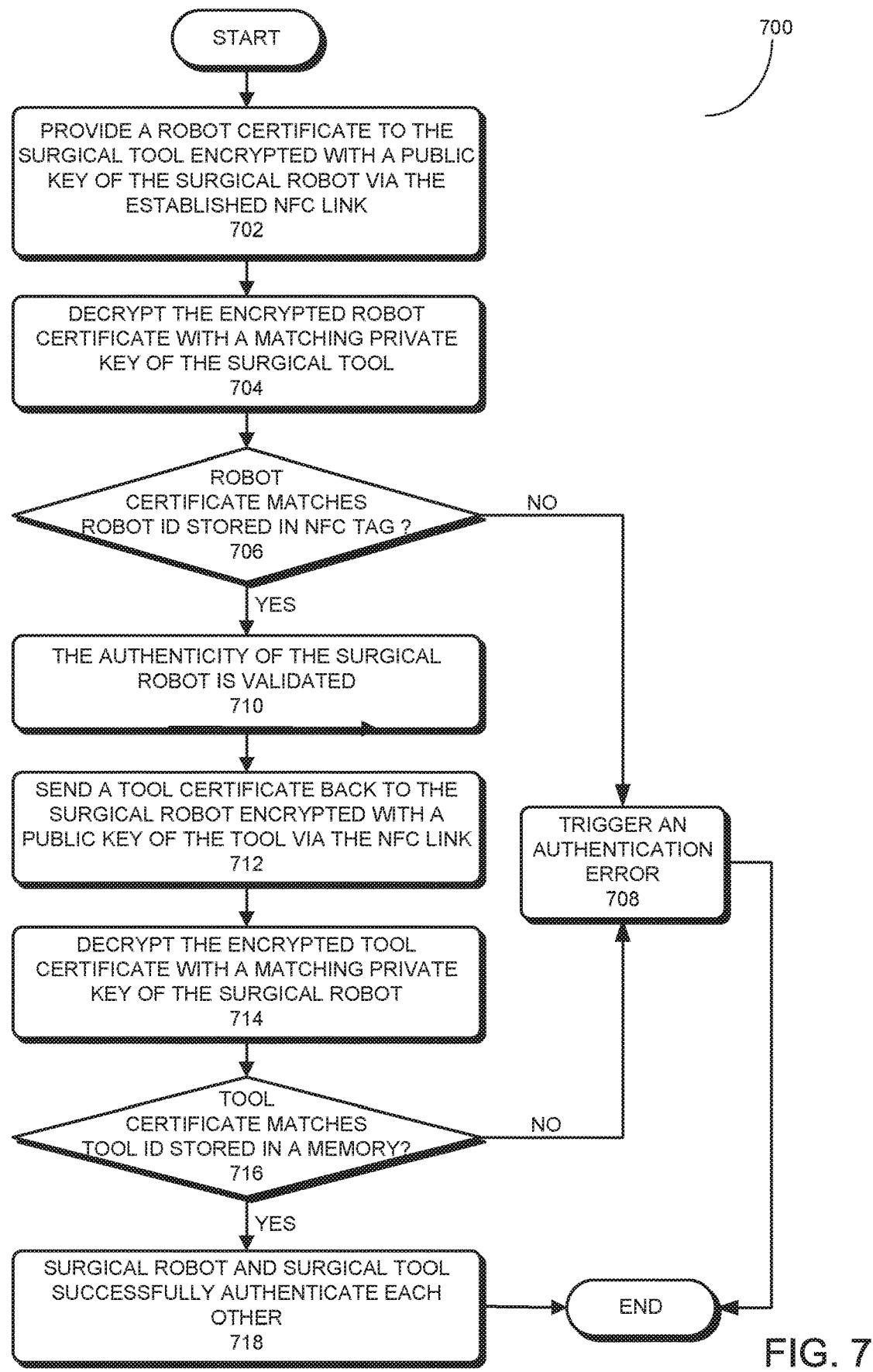
FIG. 7 presents a flowchart illustrating an exemplary process of certificate validation wherein the surgical robot and the surgical tool exchange certificates and validate each other's authenticity in accordance with some embodiments described herein.

FIG. 7 presents a flowchart illustrating an exemplary process 700 of certificate validation wherein the surgical robot and the surgical tool exchange certificates and validate each other's authenticity in accordance with some embodiments described herein. In one or more embodiments, one or more of the steps in FIG. 7 may be omitted, repeated, and/or performed in a different order. Accordingly, the specific arrangement of steps shown in FIG. 7 should not be construed as limiting the scope of the technique.

Process 700 may begin when the surgical robot provides a robot certificate to the surgical tool encrypted with a public key of the surgical robot via the established NFC link (step 702). Upon receiving the encrypted robot certificate, the surgical tool decrypts the encrypted robot certificate with a matching private key of the surgical tool (step 704). Next, surgical tool compares the received robot certificate with a robot ID stored in the NFC tag on the tool to verify if they match (step 706). If the received robot certificate does not match the stored robot ID, the certificate validation fails and an authentication error is triggered (step 708), and process 700 terminates. However, if the received robot certificate matches the stored robot ID, surgical tool validates the authenticity of the surgical robot (step 710).

Next, the surgical tool sends a tool certificate back to the surgical robot encrypted with a public key of the surgical tool via the established NFC link (step 712). Similarly, upon receiving the encrypted tool certificate, the surgical robot decrypts the encrypted tool certificate with a matching private key of the surgical robot (step 714). Next, the surgical robot compares the received tool certificate with a tool ID stored in a memory of the surgical robot to verify if they match (step 716). If the received tool certificate does not match the stored tool ID, the certificate validation fails and an authentication error is triggered (step 708), and process 700 terminates. However, if the tool certificate is successfully validated, the surgical robot and the surgical tool successfully authenticate each other and the certificate validation completes (step 718).

Figure 8:
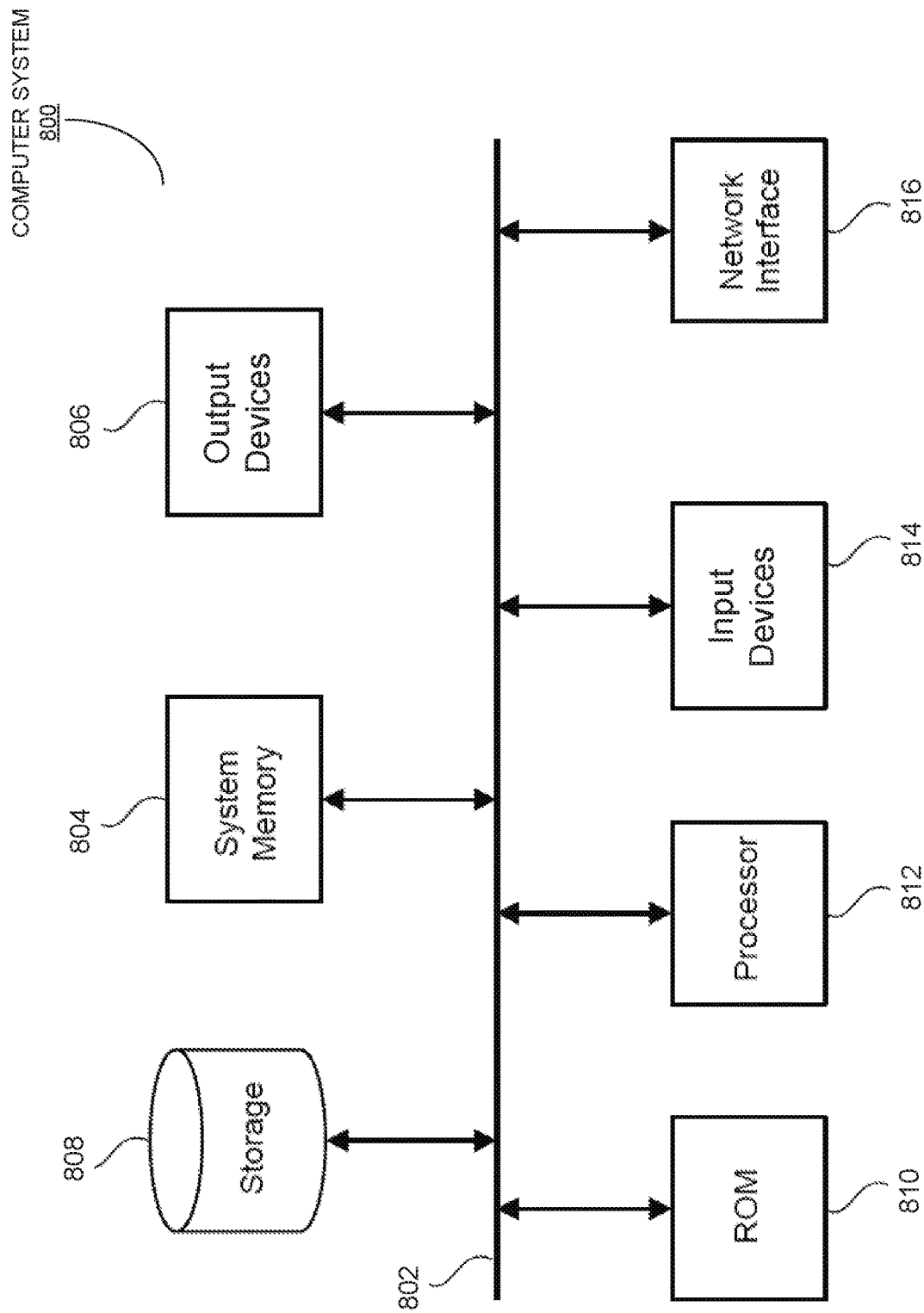
FIG. 8 conceptually illustrates a computer system with which some embodiments of the subject technology can be implemented.

FIG. 8 conceptually illustrates a computer system with which some embodiments of the subject technology can be implemented. Computer system 800 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 800 includes a bus 802, processing unit(s) 812, a system memory 804, a read-only memory (ROM) 810, a permanent storage device 808, an input device interface 814, an output device interface 806, and a network interface 816. In some embodiments, computer system 800 is a part of robotic surgical system 100.

Bus 802 collectively represents all system, peripheral, and chipset buses that communicatively connect the numerous internal devices of computer system 800. For instance, bus 802 communicatively connects processing unit(s) 812 with ROM 810, system memory 804, and permanent storage device 808.

From these various memory units, processing unit(s) 812 retrieves instructions to execute and data to process in order to execute various processes described in this patent disclosure, including the above-described processes for managing a newly-attached surgical tool on a robotic surgical system during a surgical procedure based on NFC communication in conjunction with FIGS. 5-7. The processing unit(s) 812 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 812 can be a single processor or a multi-core processor in different implementations.

ROM 810 stores static data and instructions that are needed by processing unit(s) 812 and other modules of the computer system. Permanent storage device 808, on the other hand, is a read-and-write memory device. This device is a non-volatile memory unit that stores instructions and data even when computer system 800 is off. Some implementations of the subject disclosure use a mass-storage device (such as a magnetic or optical disk and its corresponding disk drive) as permanent storage device 808.

Other implementations use a removable storage device (such as a floppy disk, flash drive, and its corresponding disk drive) as permanent storage device 808. Like permanent storage device 808, system memory 804 is a read-and-write memory device. However, unlike storage device 808, system memory 804 is a volatile read-and-write memory, such as a random access memory. System memory 804 stores some of the instructions and data that the processor needs at runtime. In some implementations, various processes described in this patent disclosure, including the above-described processes for managing a newly-attached surgical tool on a robotic surgical system during a surgical procedure based on NFC communication in conjunction with FIGS. 5-7, are stored in system memory 804, permanent storage device 808, and/or ROM 810. From these various memory units, processing unit(s) 812 retrieve instructions to execute and data to process in order to execute the processes of some implementations.

Bus 802 also connects to input and output devices 814 and 806. Input devices 814 enable the user to communicate information to and select commands for the computer system. Input devices 814 can include, for example, alphanumeric keyboards and pointing devices (also called "cursor control devices"). Output devices 806 enable, for example, the display of images generated by computer system 800. Output devices 806 can include, for example, printers and display devices, such as cathode ray tubes (CRT) or liquid crystal displays (LCD). Some implementations include devices such as a touchscreen that functions as both input and output devices.

Finally, as shown in FIG. 8, bus 802 also couples computer system 800 to a network (not shown) through a network interface 816. In this manner, the computer can be a part of a network of computers (such as a local area network ("LAN"), a wide area network ("WAN"), an intranet, or a network of networks, such as the Internet. Any or all components of computer system 800 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for automatically managing surgical tool attachment in a robotic surgical system, the method comprising:
    detecting an attachment of a surgical tool onto the robotic surgical system while a first NFC module embedded in the robotic surgical system is disabled;
    enabling the first NFC module, wherein the first NFC module when enabled, supplies wireless power to a second NFC module embedded in the surgical tool;
    establishing a secure near-field communication (NFC) link between the first NFC module and the second NFC module;
    requesting tool calibration data from the surgical tool via the secure NFC link; and
    using the received tool calibration data to initialize the surgical tool so that the surgical tool is ready for use.

2. The computer-implemented method of claim 1, wherein establishing the secure NFC link between the first NFC module in the robotic surgical system and the second NFC module in the surgical tool includes:
    transmitting a NFC link initiation request to the second NFC module; and
    receiving, at the robotic surgical system, a NFC link initiation response from the second NFC module in response to the NFC link initiation request.

3. The computer-implemented method of claim 1, wherein after establishing the secure NFC link, the method further comprises performing a certificate validation procedure between the robotic surgical system and the surgical tool to validate both an authenticity of the robotic surgical system to the surgical tool and an authenticity of the surgical tool to the robotic surgical system.

4. The computer-implemented method of claim 3, wherein performing the certificate validation procedure between the robotic surgical system and the surgical tool includes:
    providing a robot certificate to the surgical tool encrypted with a first public key of the robotic surgical system via the secure NFC link;
    at the surgical tool:
        decrypting the encrypted robot certificate with a first matching private key of the surgical tool;
        comparing the received robot certificate with a robot ID stored in the second NFC module to verify if the received robot certificate matches the stored robot ID; and
        if so, confirming the authenticity of the robotic surgical system,
        otherwise, generating a first authentication error indicating a failure of the certificate validation procedure.

5. The computer-implemented method of claim 4, wherein if the authenticity of the robotic surgical system is confirmed, the method further includes:
    sending a tool certificate to the robotic surgical system encrypted with a second public key of the surgical tool via the secure NFC link;
    at the robotic surgical system:
        decrypting the encrypted tool certificate with a second matching private key of the robotic surgical system;
        comparing the received tool certificate with a tool ID stored on the robotic surgical system to verify if the received tool certificate matches the stored tool ID; and
        if so, confirming the authenticity of the surgical tool, thereby completing the certificate validation procedure between the robotic surgical system and the surgical tool,
        otherwise, generating a second authentication error indicating a failure of the certificate validation procedure.

6. The computer-implemented method of claim 3, wherein after validating the authenticities of the robotic surgical system and the surgical tool, the method further comprises performing a session key procedure to establish a session key between the robotic surgical system and the surgical tool for secure data exchange between the robotic surgical system and the surgical tool via the secure NFC link.

7. The computer-implemented method of claim 6, wherein performing the session key procedure to establish a session key between the robotic surgical system and the surgical tool includes:
  generating a crypto challenge and a first session key;
  transmitting the crypto challenge unencrypted to the surgical tool via the secure NFC link;
  receiving, from the surgical tool, an encrypted crypto challenge encrypted with a second session key generated by the surgical tool;
  attempting to decrypt the received encrypted crypto challenge with the first session key; and
  if the decrypted crypto challenge matches the crypto challenge, establishing the first session key or the second session key as a mutual session key for encrypting data exchange between the surgical robot and the surgical tool,
  otherwise, if the decrypted crypto challenge does not match the crypto challenge, triggering an authentication error indicating a failure of the session key procedure.

8. The computer-implemented method of claim 7, wherein the crypto challenge includes a random number.

9. The computer-implemented method of claim 1, wherein prior to requesting the tool calibration data from the surgical tool, the method further comprises:
  requesting tool usability information and a tool use count from the second NFC module via the secure NFC link;
  determining if the surgical tool is usable based on the received tool usability information; and
  if the received tool usability information indicates that the surgical tool is unusable, triggering a tool identification error indicate a failure to initialize the surgical tool.

10. The computer-implemented method of claim 9, wherein if the received tool usability information indicates that the surgical tool is usable, the method further comprises:
  checking to determine if the surgical tool has been previously used in the surgical procedure; and
  if so,
    retrieving tool calibration data directly from a cache of the robotic surgical system; and
    using the retrieved tool calibration data to initialize the surgical tool so that the surgical tool is ready for use in the surgical procedure.

11. The computer-implemented method of claim 10, wherein if it is determined that the surgical tool has not been used in the surgical procedure, the method further comprises:
  decrementing the received use count of the surgical tool; and
  updating the use count of the surgical tool in the second NFC module via the established secure NFC link.

12. The computer-implemented method of claim 1, wherein the first NFC module includes an NFC reader, and wherein the second NFC module includes an NFC tag.

13. The computer-implemented method of claim 1, wherein after initializing the surgical tool, the method further includes powering down the first NFC module to save power.

14. A robotic surgical system, comprising:
  a robot arm and a first NFC module embedded in the robot arm; and
  one or more processors configured to:
    detect a surgical tool mechanically coupled to the robot arm while the first NFC module is disabled;
    enable the first NFC module, wherein the first NFC module when enabled, supplies wireless power to a second NFC module embedded in the surgical tool;
    establish a near-field communication (NFC) link between the first NFC module and the second NFC module; and
    initialize the surgical tool using tool calibration data received from the surgical tool via the established NFC link.

15. The robotic surgical system of claim 14, wherein the one or more processors are configured to establish the NFC link between the first NFC module in the robotic surgical system and the second NFC module in the surgical tool by:
  transmitting a NFC link initiation request to the second NFC module; and
  receiving, at the robotic surgical system, a NFC link initiation response from the second NFC module in response to the NFC link initiation request.

16. The robotic surgical system of claim 14, wherein the one or more processors are further configured to perform a session key procedure to establish a session key between the robotic surgical system and the surgical tool by:
  generating a crypto challenge and a first session key;
  transmitting the crypto challenge unencrypted to the surgical tool via the established NFC link;
  receiving, from the surgical tool, an encrypted crypto challenge encrypted with a second session key generated by the surgical tool;
  attempting to decrypt the received encrypted crypto challenge with the first session key; and
  if the decrypted crypto challenge matches the crypto challenge, establishing the first session key or the second session key as a mutual session key for encrypting data exchange between the surgical robot and the surgical tool,
  otherwise, if the decrypted crypto challenge does not match the crypto challenge, triggering an authentication error indicating a failure of the session key procedure.

17. The robotic surgical system of claim 14, wherein the one or more processors are further configured to:
  request tool usability information and a tool use count from the second NFC module via the established NFC link;
  determine if the surgical tool is usable based on the received tool usability information; and
  if the received tool usability information indicates that the surgical tool is unusable, trigger a tool identification error indicate a failure to initialize the surgical tool.

18. The robotic surgical system of claim 17, wherein if the received tool usability information indicates that the surgical tool is usable, the one or more processors are further configured to:
  check to determine if the surgical tool has been previously used in the surgical procedure; and
  if so,
    retrieve tool calibration data directly from a cache of the robotic surgical system; and
    use the retrieved tool calibration data to initialize the surgical tool so that the surgical tool is ready for use in the surgical procedure.

19. The robotic surgical system of claim 18, wherein if it is determined that the surgical tool has not been used in the surgical procedure, the one or more processors are further configured to:

decrement the received use count of the surgical tool; and
update the use count of the surgical tool in the second NFC module via the established NFC link.

20. The robotic surgical system of claim 18, wherein the first NFC module includes an NFC reader, and wherein the second NFC module includes an NFC tag.

* * * * *